(12) United States Patent
Shibuya

(10) Patent No.: US 10,876,288 B2
(45) Date of Patent: Dec. 29, 2020

(54) MAGNETICALLY SHIELDED ROOM

(71) Applicant: TDK Corporation, Tokyo (JP)

(72) Inventor: Tomohiko Shibuya, Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 16/480,226

(22) PCT Filed: Nov. 27, 2017

(86) PCT No.: PCT/JP2017/042452
§ 371 (c)(1),
(2) Date: Jul. 23, 2019

(87) PCT Pub. No.: WO2018/146911
PCT Pub. Date: Aug. 16, 2018

(65) Prior Publication Data
US 2019/0368191 A1 Dec. 5, 2019

(30) Foreign Application Priority Data

Feb. 13, 2017 (JP) .................................. 2017-023766

(51) Int. Cl.
*E04B 1/92* (2006.01)
*E04H 1/12* (2006.01)
(Continued)

(52) U.S. Cl.
CPC ................. *E04B 1/92* (2013.01); *E04H 1/12* (2013.01); *G01R 1/18* (2013.01); *H05K 9/0003* (2013.01);
(Continued)

(58) Field of Classification Search
CPC ........ E04B 1/92; E04B 2001/925; E04C 2/28; G01R 1/18; H05K 9/0003; E04H 1/12
See application file for complete search history.

(56) References Cited

U.S. PATENT DOCUMENTS 2,793,245 A * 5/1957 Dunn .................... H05K 9/0001
174/373
3,790,696 A * 2/1974 Lindgren ............. H05K 9/0001
174/373
(Continued)

FOREIGN PATENT DOCUMENTS

JP 55-165700 12/1980
JP 55-179395 12/1980
(Continued)

OTHER PUBLICATIONS

Translation of Shimadzu (JPS56105897) provided by Espacenet.*
International Search Report of International Application No. PCT/JP2017/042452, dated Feb. 13, 2018.

*Primary Examiner* — Patrick J Maestri
(74) *Attorney, Agent, or Firm* — Leydig, Voit & Mayer, Ltd.

(57) ABSTRACT

A magnetically shielded room, that is capable of suppressing positional deviation of a measuring tool in an internal space, has an upper shielding body, a side periphery shielding body, and a lower shielding body, which form a magnetically shielded internal space of the magnetically shielded room. A pedestal has a higher rigidity than the lower shielding body, and is located on an under surface of the lower shielding body. First and second supporting members are located on and stand erect from the pedestal. The first and second supporting members penetrate the lower shielding body and extend into the internal space.

13 Claims, 5 Drawing Sheets

1 Magnetically Shielded Room

(51) Int. Cl.
*G01R 1/18* (2006.01)
*H05K 9/00* (2006.01)
*A61B 5/04* (2006.01)
*E04C 2/28* (2006.01)

(52) U.S. Cl.
CPC ..... *A61B 5/04008* (2013.01); *E04B 2001/925* (2013.01); *E04C 2/28* (2013.01)

(56) References Cited

U.S. PATENT DOCUMENTS

| | | | |
|---|---|---|---|
| 4,794,206 A * | 12/1988 | Weinstein | H05K 9/0001 16/354 |
| 4,806,703 A * | 2/1989 | Sims | H05K 9/0001 174/373 |
| 4,959,504 A | 9/1990 | Yarger et al. | |
| 5,081,071 A * | 1/1992 | Hirschkoff | H05K 9/0001 257/E39.017 |
| 5,755,062 A * | 5/1998 | Slater | E04H 9/04 52/265 |
| 5,847,316 A | 12/1998 | Takada | |
| 6,026,975 A * | 2/2000 | Slater | B65D 90/028 220/565 |
| 6,626,264 B1 * | 9/2003 | Christen | H05K 9/0003 181/290 |
| 2005/0162249 A1 * | 7/2005 | Simola | H05K 9/0001 335/301 |
| 2008/0129068 A1 * | 6/2008 | Brummel | A61G 3/001 296/24.38 |
| 2018/0027706 A1 * | 1/2018 | Winch | E04F 15/00 174/382 |
| 2019/0177993 A1 * | 6/2019 | Shell | E04H 1/12 |
| 2020/0029474 A1 * | 1/2020 | Hawn | H05K 9/0003 |
| 2020/0037475 A1 * | 1/2020 | Rauscher | H05K 9/0003 |

FOREIGN PATENT DOCUMENTS

| | | |
|---|---|---|
| JP | 56-105897 | 8/1981 |
| JP | 2003-243875 | 8/2003 |
| JP | 2007-311523 | 11/2007 |
| JP | 2008-042128 | 2/2008 |
| JP | 2008-042128 A | 2/2008 |

\* cited by examiner

1 Magnetically Shielded Room

1 Magnetically Shielded Room

2 Magnetically Shielded Room

2 Magnetically Shielded Room

MAGNETICALLY SHIELDED ROOM

TECHNICAL FIELD

The present invention relates to a magnetically shielded room used for various magnetic measurements.

BACKGROUND ART

Patent Document 1 below discloses a magnetically shielded room for biomagnetic field measurement used in a magneto-encephalographic system for measuring a weak brain magnetic field, and a SQUID (Superconducting Quantum Interference Device) and a measuring table are installed in this magnetically shielded room.

PRIOR ART DOCUMENT

Patent Document

[Patent Document 1] Japanese Laid-Open Patent Publication No. 2007-311523

SUMMARY OF THE INVENTION

Problem to be Solved by the Invention

For instance, when a magnetically shielded room is portable and small in size, if there is vibration, the magnetically shielded room itself may shake depending on an installation location by the vibration as it is small in size. Therefore, when a measuring tool is simply placed on the floor of the magnetically shielded room, the position of the measuring tool in the magnetically shielded room is shifted.

The present invention was made in view of this situation and it is an object of the present invention to provide a magnetically shielded room that is capable of suppressing the positional deviation of a measuring tool in an internal space thereof.

Means for Solving Problem

An aspect of the present invention is a magnetically shielded room. The magnetically shielded room comprises:
an upper shielding body, a side periphery shielding body and a lower shielding body, all of which define a magnetically shielded internal space, wherein
a pedestal having a higher rigidity than the lower shielding body is located on an under surface of the lower shielding body, and a supporting member is provided erect on the pedestal, penetrates the lower shielding body and extends into the internal space.

At least part of the supporting member may contain a hollow part and the supporting member has an opening connected to the hollow part in an outer surface thereof, and wirings extend in upward or downward direction through inside of the supporting member.

The supporting member may be rod-like and a plurality of the supporting members are provided erect.

The magnetically shielded room may be movable.

It is to be noted that any arbitrary combination of the above-described structural components as well as the expressions according to the present invention changed among a system and so forth are all effective as and encompassed by the present aspects.

Effect of the Invention

According to the present invention, there is provided a magnetically shielded room that is capable of suppressing the positional deviation of a measuring tool in an internal space thereof.

EMBODIMENTS FOR CARRYING OUT THE INVENTION

Figure 1:
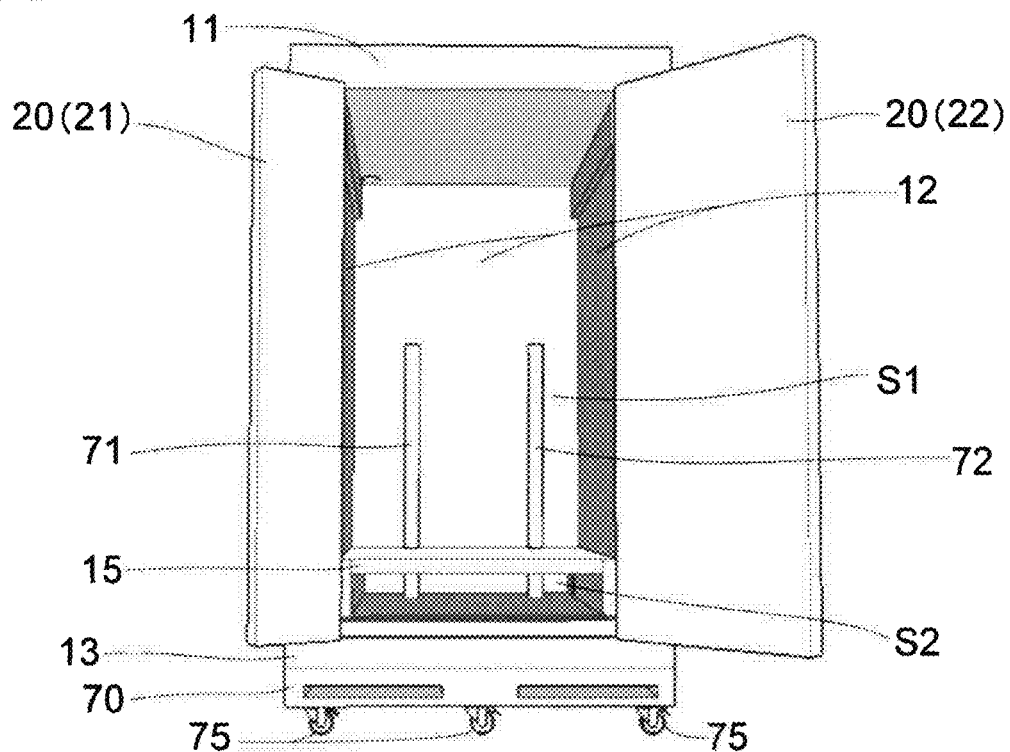
FIG. 1 is a perspective view seen from the front direction of a magnetically shielded room 1 according to a first embodiment of the present invention.

Preferred embodiments of the present invention will now be described in detail with reference to the drawings. The same or equivalent constituent parts, members, etc., shown in the drawings are designated by the same reference numerals and will not be repeatedly described as appropriate. The embodiments are not intended to limit the invention but are mere exemplifications, and all features or combinations thereof described in the embodiments do not necessarily represent the intrinsic natures of the invention.

The magnetically shielded room 1 according to the first embodiment of the present invention will be described with reference to FIGS. 1 to 8. The magnetically shielded room 1 has an upper shielding body 11, a side periphery shielding body 12, a lower shielding body 13, a door 20 for opening and closing an opening in the side wall and a partition member 15 for dividing an internal space formed by these into first and second internal spaces S1 and S2. A lid, not shown, which closes an opening on the door 20 side of the second internal space S2 and is detachable or can be opened and closed may be provided. In this case, the lid is preferably a magnetically shielding body like the partition member 15.

The partition member 15 is substantially parallel to the lower shielding body 13 and divides the above internal space into upper and lower spaces. The upper shielding body 11, the side periphery shielding body 12, the lower shielding body 13, the partition member 15 and the door 20 are magnetically shielding bodies which can shield a magnetic field noise and an electromagnetic wave noise and have, for example, a laminated panel structure formed by sandwiching a nonmagnetic material (such as timber) between a permalloy plate which is a magnetic material having high permeability and conductor and an aluminum plate which is a conductor. The permalloy plate is effective in shielding a magnetic field noise and the aluminum plate is effective in shielding a high-frequency electromagnetic wave noise. A laminate structure formed by laminating together a plurality of permalloy plates and a plurality of aluminum plates is more preferred as the shielding rate is improved. It is preferred that the conductors of the magnetically shielding bodies constituting the upper shielding body 11, the side periphery shielding body 12, the lower shielding body 13 and the partition member 15 should be electrically connected to one another. The door 20 is provided in common in the first and second internal spaces S1 and S2 and may be a single door but consists of a left door 21 and a right door 22 in this embodiment. They are connected to the left and right edge parts of the opening in the side periphery shielding body 12 by unshown hinges, respectively, in such a manner that they can open and close.

The first internal space S1 is a space surrounded by the upper shielding body 11, the partition member 15, the side periphery shielding body 12 and the closed door 20. The first internal space S1 has a larger capacity than the second internal space S2, and an unshown measurement object to be measured, measurement equipment (metering equipment) such as magnetic sensors 83 (FIG. 6) for measuring the magnetism of the measurement object and a measurement jig 80 for holding the measurement equipment are installed in this space. The support of the measurement jig 80 will be described hereinafter. The second internal space S2 is a space surrounded by the lower shielding body 13, the partition member 15, lower parts of the side periphery shielding body 12 and the closed door 20 (or the above unshown lid). The second internal space S2 has a smaller capacity than the first internal space S1, and unshown supplementary equipment (a power unit, measurement control units, etc.) are installed in this space. The supplementary equipment may be installed outside the magnetically shielded room 1. In this case, the number of the internal spaces of the magnetically shielded room 1 may be one by omitting the partition member 15.

Figure 8:
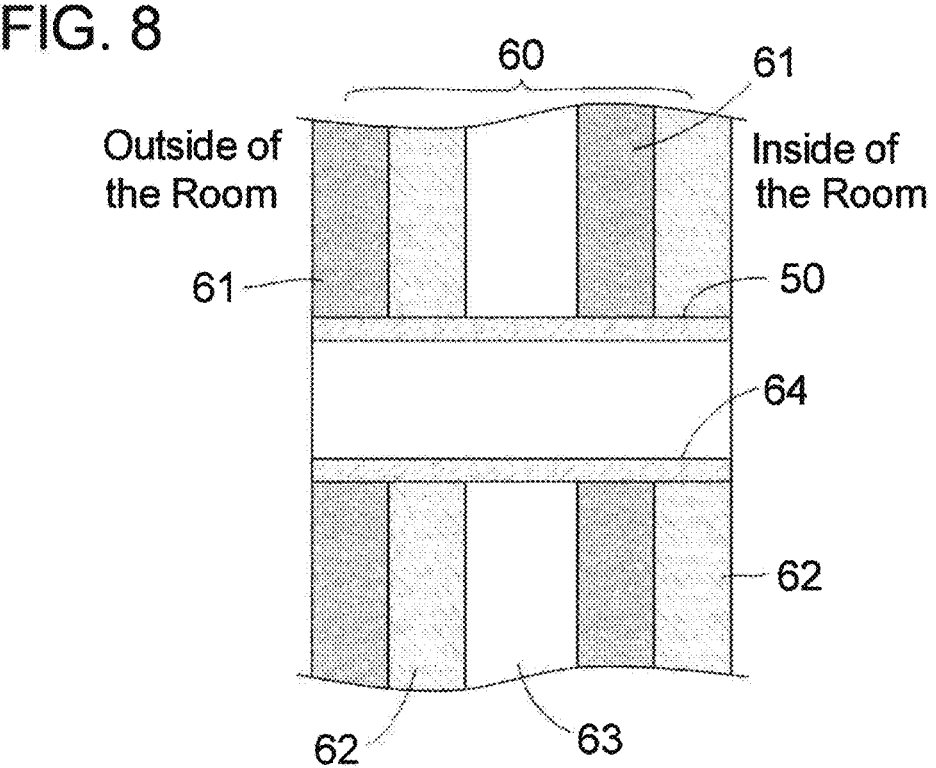
FIG. 8 is a sectional view of a part around a through hole 50 in the shielding body of the magnetically shielded room 1.

A through hole 50 for letting wirings connected to the unshown measurement equipment and the power cords and cables of the unshown supplementary equipment pass therethrough is formed in either one of the upper shielding body 11, the side periphery shielding body 12 and the lower shielding body 13. As shown in FIG. 8, the upper shielding body 11, the side periphery shielding body 12, the lower shielding body 13 and the partition member 15 are laminated panels 60 manufactured by laminating together permalloy plates 61, aluminum plates 62 and a nonmagnetic material 63 such as timber, and a pipe-like through conductor 64 is provided on at least part of the inner wall of the through hole 50 penetrating the laminated panel 60. The permalloy plate 61 and the aluminum plate 62 on the inner side of the laminated panel 60 are made conductive to the permalloy plate 61 and the aluminum plate 62 on the outer side by the pipe-like through conductor 64 to have the same potential. The material of the pipe-like through conductor 64 is, for example, aluminum, copper or permalloy.

A pedestal 70 having the same size as the bottom surface of the lower shielding body 13 and a higher rigidity than the lower shielding body 13 is provided below (under surface) the lower shielding body 13 to mount and fix the lower shielding body 13 thereon. The pedestal 70 is made of, for example, stainless steel. At least three casters 75 with a stopper are attached to the bottom surface of the pedestal 70 as moving means for moving over the floor. The magnetically shielded room 1 is movable and provided with the castors 75, which is convenient at the time of moving. The upper shielding body 11, the side periphery shielding body 12, the lower shielding body 13 and the partition member 15 are conductively connected to the pedestal 70 (electrically connected to have the same potential). The pedestal 70 may be made of a nonmagnetic material having high stiffness and non-conductivity.

Figure 5:
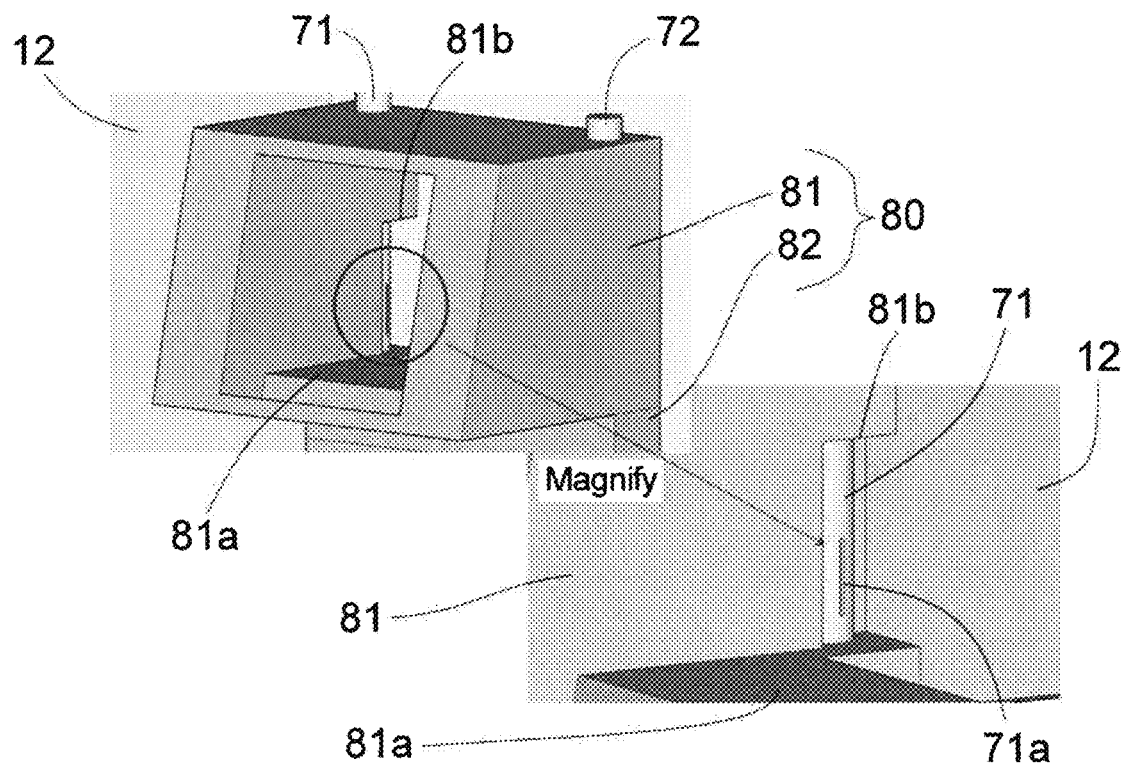
FIG. 5 is an enlarged view of a key part around the measurement jig 80 in FIG. 2.
Figure 6:
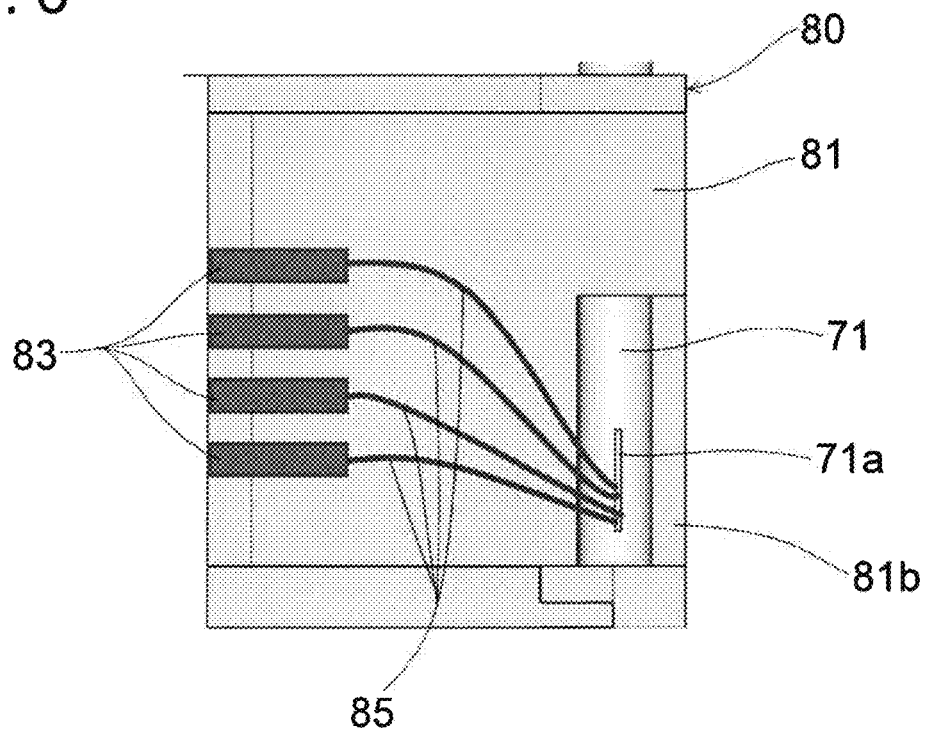
FIG. 6 is an enlarged sectional side view of the key part of FIG. 5 showing that the wirings 85 of magnetic sensors 83 held by the measurement jig 80 enter the inside of the support member 71 from an opening 71a of the support member 71.
Figure 7:
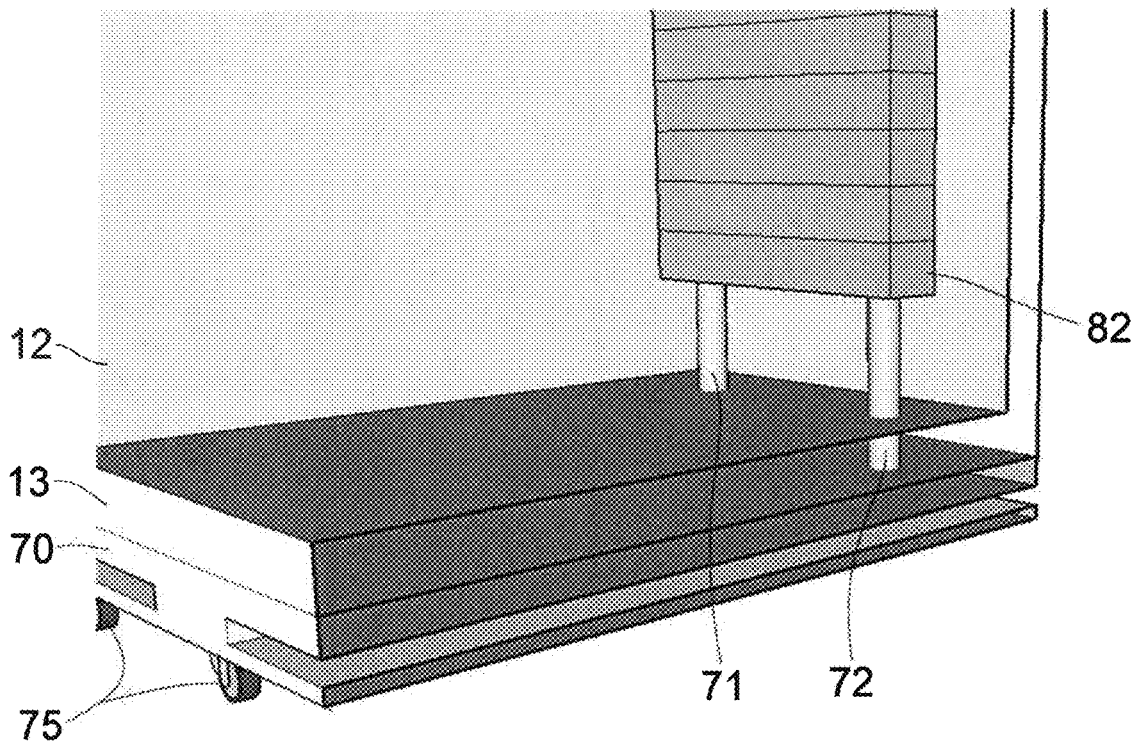
FIG. 7 is an enlarged perspective sectional view of the key part showing the enlarged lower part of the magnetically shielded room 1 and a lower shielding body 13 partially made transparent so that the lower end part (part entering the screw hole of a pedestal 70) of the support member 72 can be seen while a partition member 15 is omitted.

Two supporting members 71 and 72 are provided erect on the pedestal 70 and extend upward. The supporting members 71 and 72 are made of a material having a higher rigidity than the upper shielding body 11, the side periphery shielding body 12 and the lower shielding body 13, for example, a nonmagnetic metal such as nonmagnetic stainless steel. The supporting members 71 and 72 are rod-like with an outer peripheral wall having a cylindrical side face shape, and the lower ends thereof are screws which are screwed into screw holes in the pedestal 70 to be fixed. The means of fixing (attaching) the supporting members 71 and 72 to the pedestal 70 is not limited to thread connection and may be another fixing (attaching) means such as press-in. The supporting members 71 and 72 penetrate the lower shielding body 13 and extend into the second internal space S2 and further penetrate the partition member 15 and extend into the first internal space S1. The supporting member 71 is hollow and has an opening 71a connected to the hollow part in the outer peripheral wall as shown in FIG. 5. Wirings 85 which will be described hereinafter extend in vertical direction through the inside of the supporting member 71. The supporting member 72 may be hollow or non-hollow. When the supporting member 72 is hollow, the same material as the supporting member 72 or a material having a higher rigidity than the above material may be buried in the inside of the supporting member 72. In this case, the strength of the supporting member 72 is improved and even when the weights of the measurement jig 80 and the measurement equipment such as the magnetic sensors 83 supported thereby are large, they can be surely fixed. When the wirings 85 are not let pass through the supporting member 71, the supporting member 71 may be constituted the same as the supporting member 72.

Figure 2:
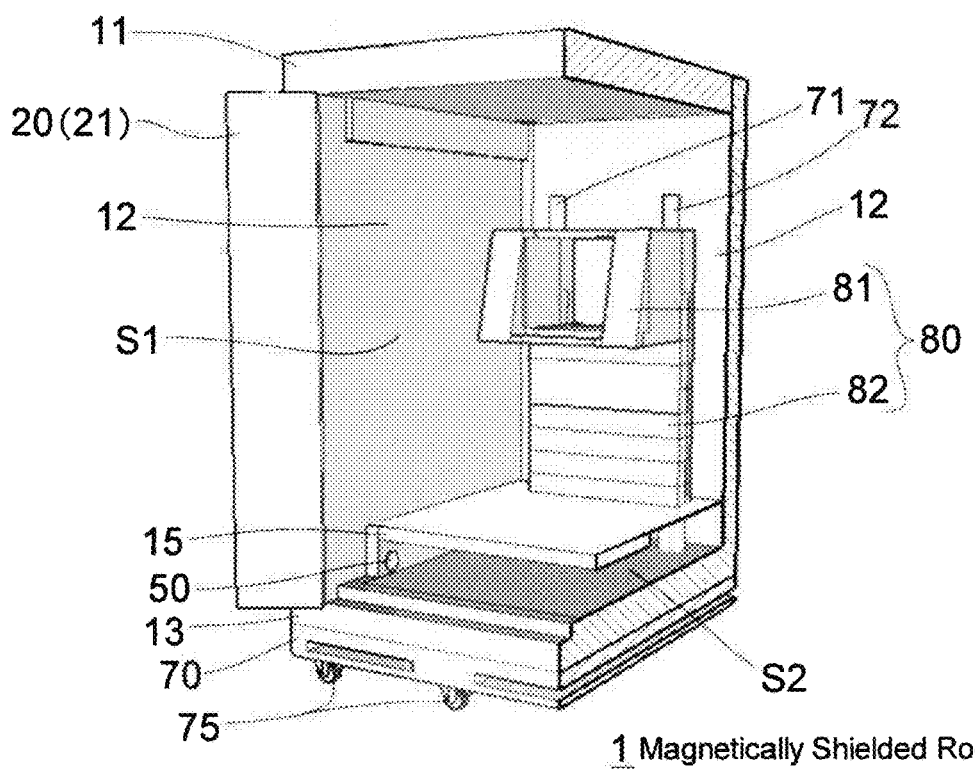
FIG. 2 is a perspective sectional view of the magnetically shielded room 1 in which a measurement jig 80 is attached to support members 71 and 72.
Figure 3:
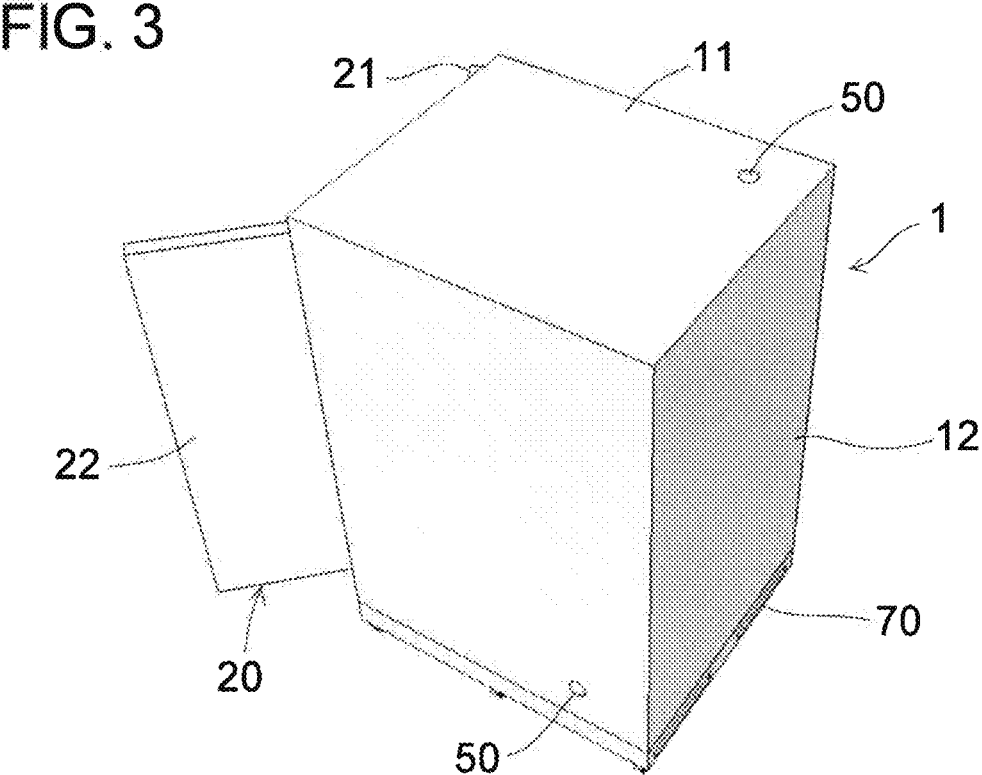
FIG. 3 is a perspective view seen from the rear upper right direction of the magnetically shielded room 1.
Figure 4:
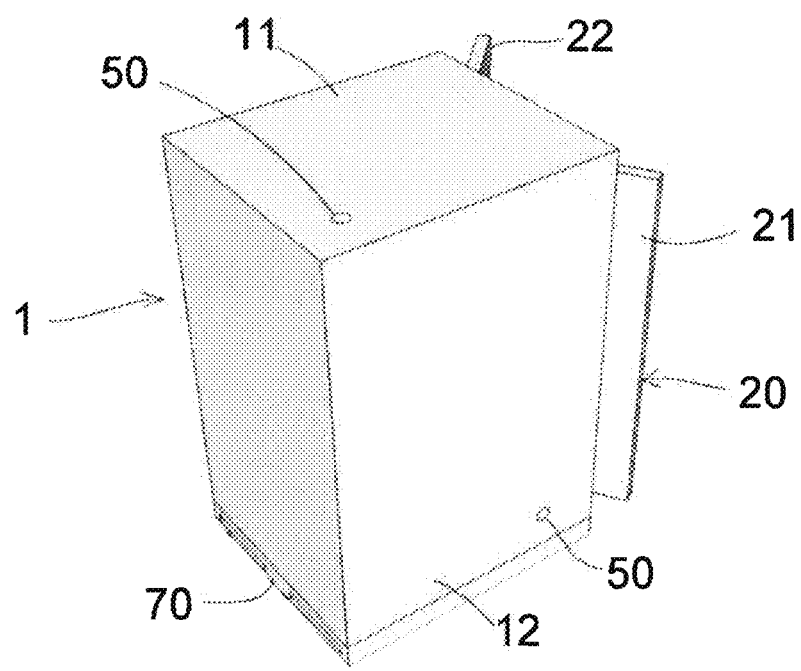
FIG. 4 is a perspective view seen from the rear upper left direction of the magnetically shielded room 1.

The supporting members 71 and 72 are used to fix the position of the measurement jig 80 in the magnetically shielded room 1. The measurement jig 80 is made of a nonmagnetic material, for example, a plastic material such as acryl or timber. As shown in FIG. 2, the measurement jig 80 has a jig body 81 and a plurality of spacers 82. The spacers 82 are substantially rectangular and have through holes for letting the supporting members 71 and 72 pass therethrough, respectively. The height of the jig body 81 can be adjusted by the number of the spacers 82. The jig body 81 holds the magnetic sensors 83 (FIG. 6) as measuring instruments and has through holes for letting the supporting members 71 and 72 pass therethrough, respectively. The jig body 81 has a holding stand 81a for holding the magnetic sensors 83 and further a notch 81b for exposing the opening 71a of the supporting member 71. The wirings 85 extending from the magnetic sensors 83 are leaded to the inside of the supporting member 71 through the notch 81b and the opening 71a. The wirings 85 may be connected to the unshown supplementary equipment installed in the second internal space S2 or drawn to the outside of the magnetically shielded room 1.

When the magnetically shielded room 1 is used, the unshown supplementary equipment are installed in the second internal space S2 and the measurement equipment such as the magnetic sensors 83 are installed in the first internal space S1. Then, the unshown measurement object to be measured is placed in the first internal space S1 and the left door 21 and the right door 22 constituting the door 20 are closed. As a result, the first internal space S1 is magnetically shielded from the outside and prevents the intrusion of a magnetic field noise and an electromagnetic wave noise from the outside, thereby making it possible to carry out necessary magnetic measurements.

According to this embodiment of the present invention, the following effects can be obtained.

(1) Since the pedestal 70 having a higher rigidity than the lower shielding body 13 is provided on the under surface of the lower shielding body 13 and the supporting members 71 and 72 are provided erect on the pedestal 70, measuring tools can be supported (fixed) in the magnetically shielded room 1 by using the supporting members 71 and 72 and the positional deviations of the measuring tools can be suppressed even when the magnetically shielded room 1 is portable or small in size. The measuring tools include the measurement equipment such as the magnetic sensors 83 and the measurement jig 80 for supporting them and may include a table for mounting the measurement object and other objects related to measurement as required.

(2) When the supporting members 71 and 72 are provided on the upper shielding body 11, the side periphery shielding body 12 or the lower shielding body 13, the shielding body made of permalloy is apt to be deformed, whereby positional deviation caused by deformation and the deterioration of magnetic shield performance are concerned. However, since the supporting members 71 and 72 are provided erect on the pedestal 70 having a higher rigidity than the shielding body in this embodiment, positional deviation caused by deformation and the deterioration of magnetic shield performance are suppressed.

(3) Since the measuring tools are supported by the two supporting members 71 and 72, even when the supporting members 71 and 72 are round rods or round pipes which are easily acquired and the through holes of the measurement jig 80 for letting the supporting members 71 and 72 pass therethrough are round holes which are easily processed, the turning of the measurement jig 80 can be prevented.

(4) Since one or more through holes 50 are formed in either one of the upper shielding body 11, the side periphery shielding body 12, the lower shielding body 13 and the partition member 15, they are convenient for wiring work. The through conductor 64 is provided on at least part of the inner wall of the through hole 50 to be made conductive to the conducting plates (the permalloy plates 61 and the aluminum plates 62) of the upper shielding body 11, the side periphery shielding body 12, the lower shielding body 13 or the partition member 15, thereby making it possible to reduce the leakage of an electromagnetic wave noise from the through hole 50.

(5) By mounting and fixing the body part of the magnetically shielded room including the upper shielding body 11, the side periphery shielding body 12 and the lower shielding body 13 on the pedestal 70 having high stiffness, the weight of the bottom surface of the above body part is dispersed and stabilized, thereby making it possible to reduce the distortion of the magnetically shielded room 1 at the time of moving.

(6) When the pedestal 70 is a conductor, grounding is easily made at the time of fixing the magnetically shielded room 1 by electrically connecting the upper shielding body 11, the side periphery shielding body 12 and the lower shielding body 13 (that is, the body part of the magnetically shielded room) to the pedestal 70. That is, the pedestal 70 should be connected to an external ground connection terminal.

Second Embodiment

Figure 9:
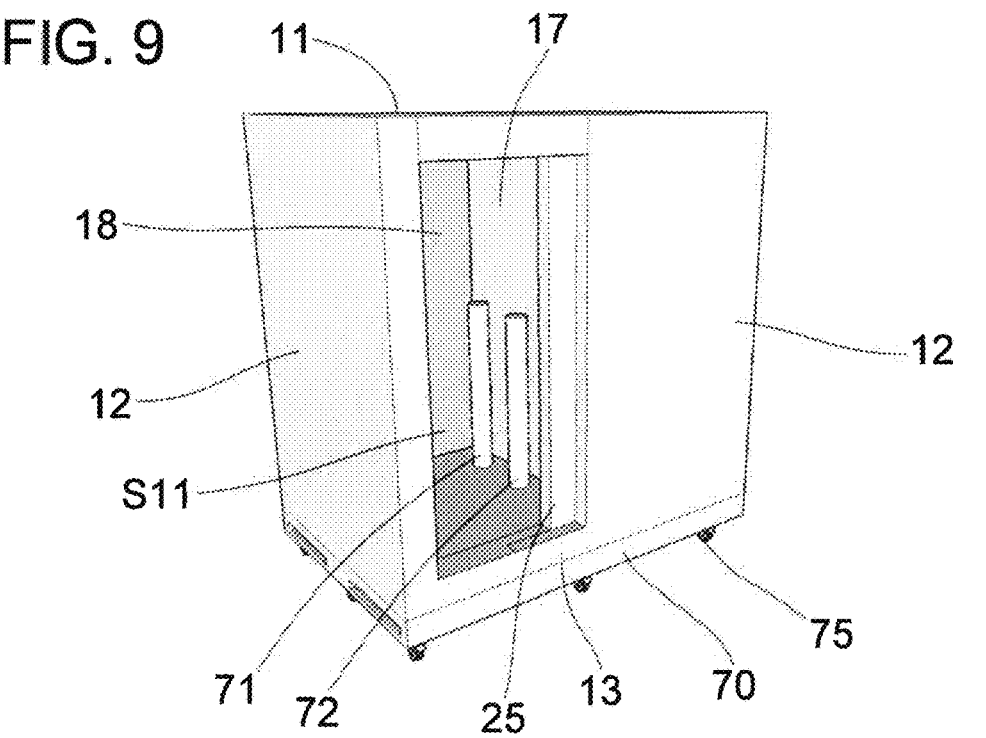
FIG. 9 is a perspective view seen from the front upper left direction of a magnetically shielded room 2 according to a second embodiment of the present invention.
Figure 10:
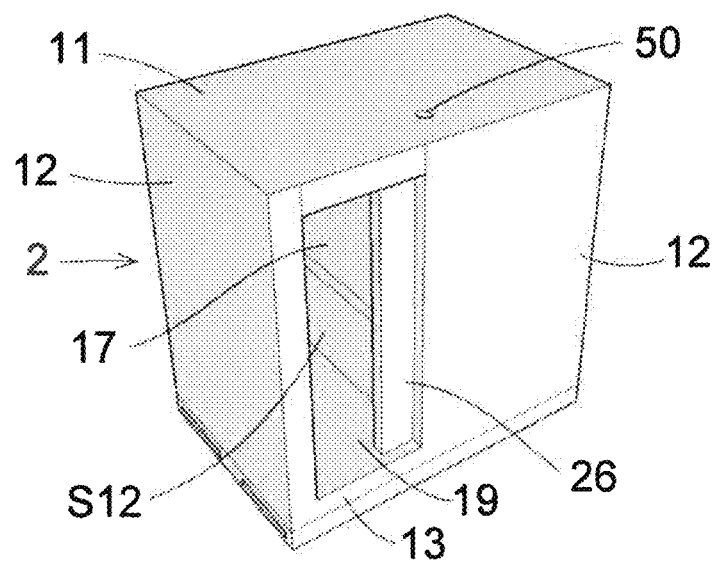
FIG. 10 is a perspective view seen from the rear upper right direction of the magnetically shielded room 2.

FIG. 9 is a perspective view seen from the front upper left direction of a magnetically shielded room 2 according to a second embodiment of the present invention. FIG. 10 is a perspective view seen from the rear upper right direction of the magnetically shielded room 2. The magnetically shielded room 2 has an upper shielding body 11, a side periphery shielding body 12, a lower shielding body 13, doors 25 and 26 for opening and closing openings 18 and 19 in the side wall formed on the front side and the rear side, respectively, and further a partition member 17 for dividing an internal space formed by these into first and second internal spaces S11 and S12. The partition member 17 is substantially parallel to the side periphery shielding body 12 and divides the above internal space into right and left spaces. The upper shielding body 11, the side periphery shielding body 12, the lower shielding body 13, the partition member 17 and the doors 25 and 26 are magnetically shielding bodies which can shield a magnetic field noise and an electromagnetic wave noise and have, for example, a laminated panel structure formed by sandwiching a non-magnetic material (such as timber) between a permalloy plate which is a magnetic material having high permeability and conductor and an aluminum plate which is a conductor (the same as in the first embodiment). The door 25 closes the opening 18 in the side wall of the first internal space S11 and is a sliding door which opens and closes the opening 18 in the side wall located on the front side of the magnetically shielded room 2. The door 26 closes the opening 19 in the side wall of the second internal space S12 and is a sliding door which opens and closes the opening 19 in the side wall on the rear side of the magnetically shielded room 2. The doors 25 and 26 may be revolving doors in place of sliding doors.

The first internal space S11 is a space surrounded by the upper shielding body 11, the side periphery shielding body 12, the lower shielding body 13, the partition member 17 and the closed door 25. The second internal space S12 is a space surrounded by the upper shielding body 11, the side periphery shielding body 12, the lower shielding body 13, the partition member 17 and the closed door 26. For example, the measurement object to be measured is placed in the first internal space S11 and the measurement equipment such as the magnetic sensors for measuring the measurement object are arranged in the second internal space S12.

Like the first embodiment, a through hole 50 for letting wirings connected to the magnetic sensors for measuring the measurement object 30 and the power cords and cables of supplementary equipment such as a power unit and measurement control units pass therethrough is formed in either one of the upper shielding body 11, the side periphery shielding body 12, the lower shielding body 13 and the partition member 17. As shown in FIG. 8, a pipe-like through conductor 64 is provided on the inner wall of the throughhole 50. Like the first embodiment, a pedestal 70 is provided on the under surface of the lower shielding body 13, at least three casters 75 with a stopper are attached to the bottom surface of the pedestal 70, and two supporting members 71 and 72 are provided erect on the pedestal 70 and extend into the first internal space S11.

Since the magnetically shielded room 2 of the second embodiment has the first and second internal spaces S11 and S12 on the right and left sides, respectively, the internal spaces S11 and S12 can be made large in height and therefore are suitable for storing a tall measurement object to be measured and high supplementary equipment. Other constitution and function and effect of the second embodiment are the same as those of the first embodiment.

While the invention has been described in its preferred embodiments, it is to be understood by a person having ordinary skill in the art that variations may be made on each constituent element and process of the embodiments without departing from the scope of the following claims. Variations of the invention will be described hereinafter.

The supporting members 71 and 72 are not limited to those with an outer peripheral wall having a cylindrical side face shape and may be a square rod or square pipe and further not limited to rod-like or pipe-like supporting members. The number of supporting members is not limited to two and may be one, or three or more. The supporting members 71 and 72 are not limited to those extending in a vertical direction (direction perpendicular to the top surface of the lower shielding body 13) and may be obliquely inclined, not parallel to each other or cross each other. The attachment of the supporting members 71 and 72 to the measurement jig 80 is carried out not only by letting the supporting members 71 and 72 pass through the through holes of the measurement jig 80 but also by attachment with a supporting tool such as a bracket.

Although the appearance of the magnetically shielded room is rectangular, it may be cylindrical. For example, it may have a structure that the internal space of a hollow cylinder is divided into upper and lower spaces or right and left spaces by a partition member. The internal space may be divided into three or more spaces by a plurality of partition members. Although the doors are provided on the front side and rear side of the magnetically shielded room in the second embodiment, respectively, if the openings of the divided internal space can be opened and closed individually, the arrangement of the doors is arbitrary. The doors in the above embodiments are not limited to revolving doors or sliding doors and may have any structure if they can open and close the openings of the internal space.

EXPLANATION OF NUMERALS

1,2 magnetically shielded room, 11 upper shielding body, 12 side periphery shielding body, 13 lower shielding body, 15,17 partition member, 20,25,26 door, 50 through hole, 60 laminated panel, 70 pedestal, 71,72 supporting member, 71a opening, 75 caster with a stopper, 80 measurement jig, 81 jig body, 81a holding stand, 81b notch, 82 spacer, 83 magnetic sensor, 85 wiring, S1, S11 first internal space, S2, S12 second internal space

The invention claimed is:

1. A magnetically shielded room comprising:
an upper shielding body;
a side periphery shielding body;
a lower shielding body, wherein the upper shielding body, the side periphery shielding body, and the lower shielding body define a magnetically shielded internal space of the magnetically shielded room;
a pedestal having a higher rigidity than the lower shielding body and located on an under surface of the lower shielding body;
a supporting member located on and standing erect from the pedestal, penetrating the lower shielding body, and extending into the internal space; and
a partition member located within the internal space and dividing the internal space into first and second internal spaces, wherein the supporting member penetrates through the partition member.

2. The magnetically shielded room according to claim 1, wherein
the supporting member has an outer surface, contains a hollow part, and has an opening in the outer surface communicating with the hollow part, and
the magnetically shielded room further includes wirings extending in an upward direction or a downward direction through the hollow part and the opening of the supporting member.

3. The magnetically shielded room according to claim 1, further including a plurality of the supporting members located on and standing erect from the pedestal, wherein at least one of the supporting members is a rod.

4. The magnetically shielded room according to claim 1, wherein the magnetically shielded room is movable.

5. The magnetically shielded room according to claim 2, further including a plurality of the supporting members located on and standing erect from the pedestal, wherein at least one of the supporting members is a rod.

6. A magnetically shielded room comprising:
an upper shielding body;
a side periphery shielding body;
a lower shielding body, wherein the upper shielding body, the side periphery shielding body, and the lower shielding body define a magnetically shielded internal space of the magnetically shielded room;
a pedestal located on an under surface of the lower shielding body;
a supporting member having a lower end penetrating through the lower shielding body and located in and attached to the pedestal, and an upper end standing upright from the pedestal and the lower shielding body and located within the internal space, extending beyond the lower shielding body, toward the upper shielding body; and
a partition member dividing the internal space into first and second internal spaces, wherein the supporting member penetrates through the partition member.

7. The magnetically shielded room according to claim 6, wherein
the supporting member has an outer surface, contains a hollow part, and has an opening in the outer surface communicating with the hollow part, and
the magnetically shielded room further includes wirings extending through the hollow part and the opening of the supporting member.

8. The magnetically shielded room according to claim 6, further including two of the supporting members, wherein one of the supporting members is a rod.

9. The magnetically shielded room according to claim 6, further including a plurality of casters for rolling across a floor and attached to an underside of the pedestal so that the pedestal is between the plurality of casters and the lower shielding body, wherein the magnetically shielded room is movable across the floor via the plurality of casters.

10. A magnetically shielded room comprising:
an upper shielding body;
a side periphery shielding body;
a lower shielding body, wherein the upper shielding body, the side periphery shielding body, and the lower shielding body define a magnetically shielded internal space of the magnetically shielded room;
a pedestal located on an under surface of the lower shielding body; and
a supporting member having a lower end penetrating through the lower shielding body and located in and attached to the pedestal, and an upper end standing upright from the pedestal and the lower shielding body and located within the internal space, extending beyond the lower shielding body, toward the upper shielding body, wherein
the supporting member has an outer surface, contains a hollow part, and has an opening in the outer surface communicating with the hollow part, and
the magnetically shielded room further includes wirings extending through the hollow part and the opening of the supporting member.

11. The magnetically shielded room according to claim 10, further including a partition member located within the internal space and dividing the internal space into first and second internal spaces.

12. The magnetically shielded room according to claim 11, further including two of the supporting members, wherein one of the supporting members is a rod.

13. The magnetically shielded room according to claim 11, further including a plurality of casters for rolling across a floor and attached to an underside of the pedestal so that the pedestal is between the plurality of casters and the lower shielding body, wherein the magnetically shielded room is movable across the floor via the plurality of casters.

* * * * *